United States Patent [19]
Superak

[11] Patent Number: 5,959,184
[45] Date of Patent: Sep. 28, 1999

[54] PLANTS AND SEEDS OF *CUCURBITA PEPO* HAVING A GENETIC FACTOR FOR SPINELESSNESS

[75] Inventor: Theodore H. Superak, Davis, Calif.

[73] Assignee: Harris Moran Seed Company, Modesto, Calif.

[21] Appl. No.: 08/767,223

[22] Filed: Dec. 13, 1996

[51] Int. Cl.$^6$ .............................. A01H 5/00; A01H 5/10; A01H 1/04
[52] U.S. Cl. ..................... 800/310; 800/298; 800/260
[58] Field of Search ........................ 800/200, 250, 800/255, DIG. 18, DIG. 20, DIG. 21, 298, 310, 260; Plt./258

[56] References Cited

PUBLICATIONS

Ahmed et al. Resistance to three isolates of zucchini yellow mosaic virus (ZYMV) in squash (*Cucurbita pepo* L.) Report—Cucurbit Genetics Cooperative, No. 19. pp. 81–82. (Abstract only), 1996.
Stokes Grower Guide (Seed Catalog) Entry 'Spineless Beauty' p. 47, 1991.
Thomas & Morgan Inc., The Seed Catalogue. Entry 'Spineless Beauty' p. 184, 1993.
Van Eseltine, *Proc. Am. Soc. Hort. Sci.* 34:577–581 (1937).
Erwin, *Proc. Am. Soc. Hort. Sci.* 24:71–72 (1927).
Castetter, E.F., *American Society for Horticultural Science*, 338–340 (1925).
A. Korzeniewska, 1992, Newgenes in *Cucurbita Maxima* In: 5th Eucarpia Cucurbitaceae Symposium. Skierniewice, Poland, p. 75.
Rogers NK Seed Co., P.O. Box 4188, Boise, Idaho 83711, "Vegetable Seed Guide", p. 68 (1992).
Holton, Melissa L., "Inheritance of Spininess in Summer Squash", Master of Science Thesis in Vegetable Crops in the Graduate Division of the University of California Davis- (complete thesis) (1980).
Korzeniewska, A. New Genes in *Cucurbita Maxima* Duch. from Proceedings of Fifth Eucarpia Cucurbitaceae Symposium, pp. 75–78, Jul. 27–31, 1992.

*Primary Examiner*—Douglas W. Robinson
*Assistant Examiner*—Melissa L. Kimball
*Attorney, Agent, or Firm*—Rothwell, Figg, Ernst & Kurz

[57] ABSTRACT

The present invention relates generally to plants and seeds having a genetic factor conferring onto *Cucurbita pepo* a spineless phenotype in the homozygous state and a semi-spineless phenotype in the heterozygous state and methods for introducing the genetic factor into plants.

11 Claims, 3 Drawing Sheets

PLANTS AND SEEDS OF *CUCURBITA PEPO* HAVING A GENETIC FACTOR FOR SPINELESSNESS

FIELD OF THE INVENTION

The present invention relates generally to plants and seeds having a genetic factor conferring onto *Cucurbita pepo* a spineless phenotype in the homozygous state and a semispineless phenotype in the heterozygous state and methods for introducing the genetic factor into plants.

BACKGROUND OF THE INVENTION

The squash family includes a variety of different domesticated plant species, namely *Cucurbita pepo, C. moshata,* and *C. maxima*. These vegetables are of significant economic importance as they encompass many coveted summer and winter edible types as well as ornamental gourds. *Cucurbita pepo* L. refers to what is commonly known as the summer squash such as scallop, zucchini, straightneck and crookneck types and winter squash such as acorn and pumpkin.

*Cucurbita pepo* like other squash comprise stiff spines or trichomes which are located along the midribs on the abaxial leaf surface and along the length of the petiole as well as along other plant parts. *C. pepo* is described as including varieties which are "harsh prickly plants," Van Eseltine, Proc. Am. Soc. Hort. Sci. 34:577–581 (1937). See also, Erwin, Proc. Am. Soc. Hort. Sci. 24:71–72 (1927). These spines are commercially disadvantageous for at least two reasons. They are rough and scratchy to the touch which is problematic since the fruits are generally hand harvested. The scratchy feel of the plant is uncomfortable, irritates the skin and can discourage efficient picking. Further, spines damage the fruit as the fruit comes into contact with them when picked. This damage can result in scarring and water loss which makes the fruit less appealing to the consumer. Thus, development of plant lines without such spines would be well-received by both growers and consumers.

SUMMARY OF THE INVENTION

This invention provides a newly identified genetic factor originally derived from *Cucurbita pepo* that confers onto *Cucurbita pepo* a spineless phenotype in the homozygous state and a semispineless phenotype in the heterozygous state, plants and seeds containing such factor and methods for introducing the genetic factor into plants.

All three photographs referred to above were taken at the same magnification and represent individuals from the same F2 population.

Figure 4A:
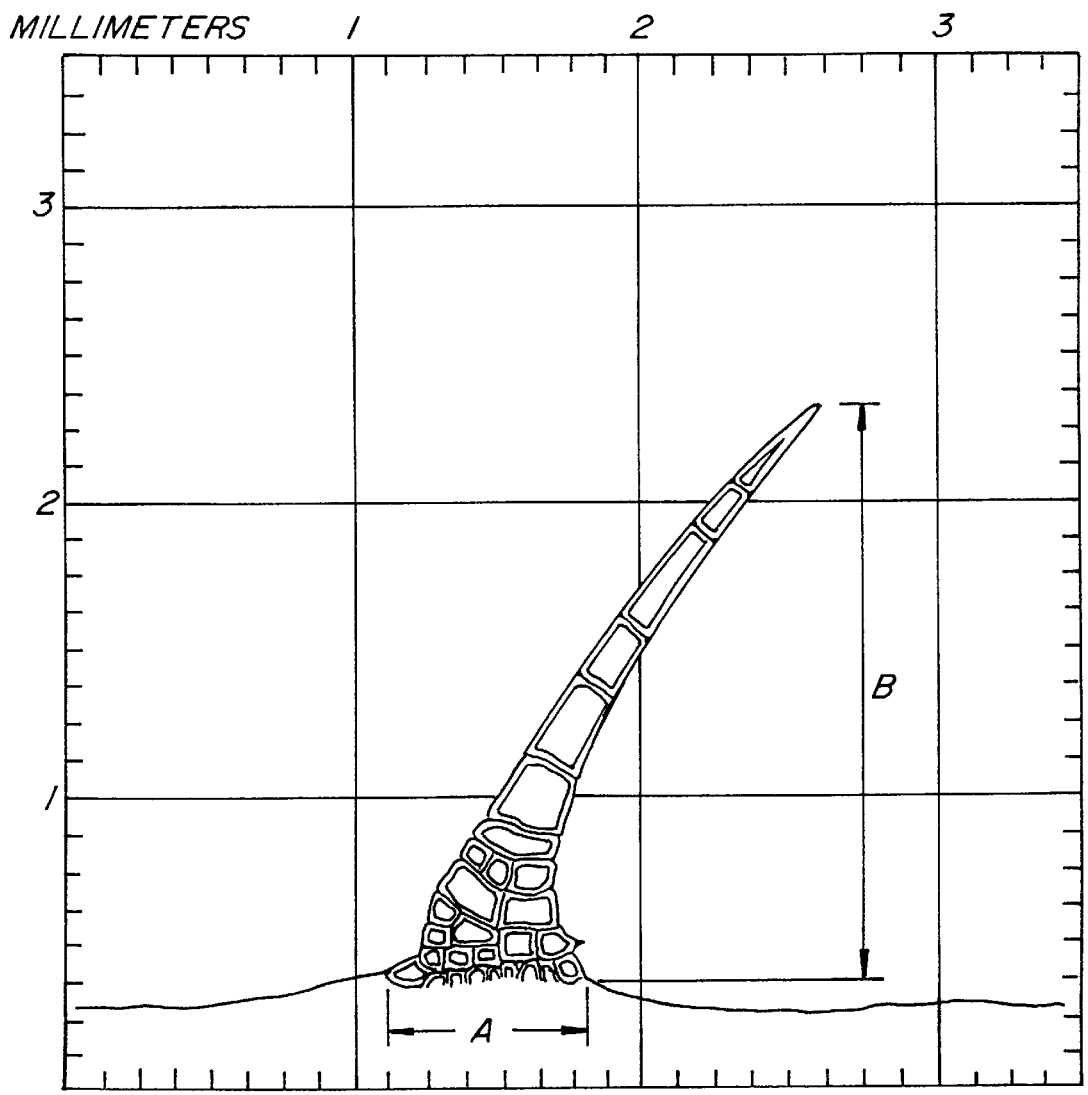
Figure 4B:
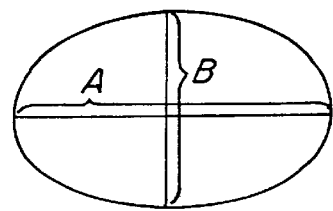

FIGS. 4A and 4B illustrate lengthwise cross-sections of a spine or trichome and the location of measurements which can be made to compare the size of spines. FIG. 4A represents a lengthwise cross-section of a typical spine and FIG. 4B represents a diagrammatic cross-section of the base of the spine with a major axis (A) and a minor axis (B).

DETAILED DESCRIPTION

This invention provides a genetic factor conveying spinelessness on plants, particularly *Cucurbita pepo*, which advantageously decreases the discomfort felt by fruit pickers and others handling the subject plants and which improves the appearance of the fruit to the consumer.

The subject genetic factor is a genetic factor which confers spinelessness on a plant of interest, preferably *Cucurbita pepo* in the homozygous state. It is controlled by a single allele which in a homozygous state results in a spineless plant and in a heterozygous state exhibits incomplete dominance that results in a semispineless plant.

Figure 1:
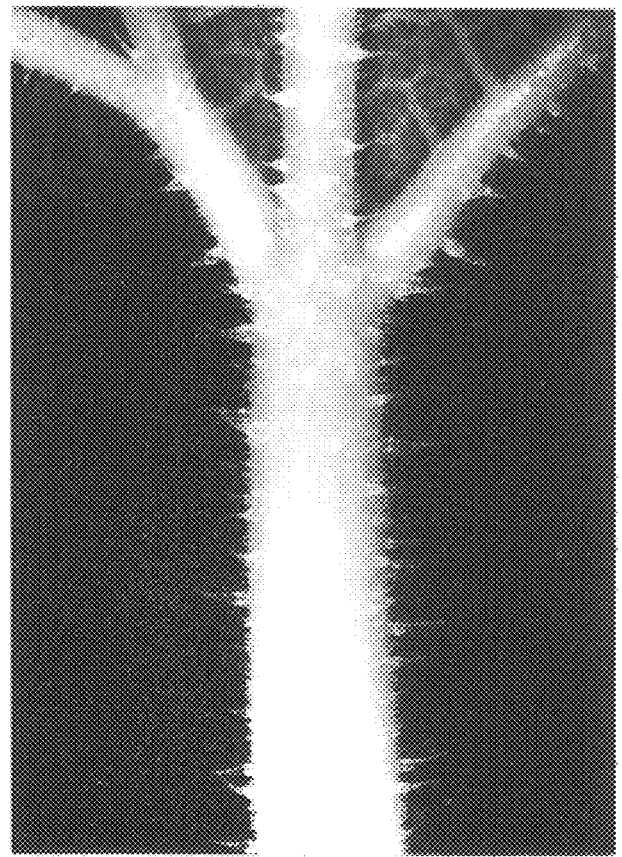
FIG. 1 is a photograph of a spiney petiole of *C. pepo* which does not have the genetic factor for the spineless phenotype.
Figure 2:
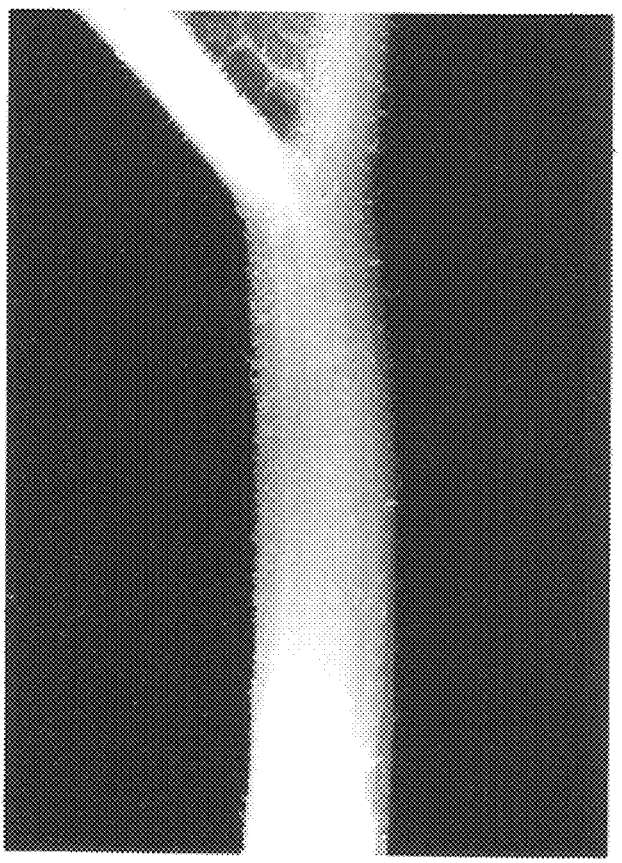
FIG. 2 is a photograph of a spineless petiole of *C. pepo* in which the genetic factor for the spineless phenotype described herein has been introduced and exists in the homozygous state.
Figure 3:
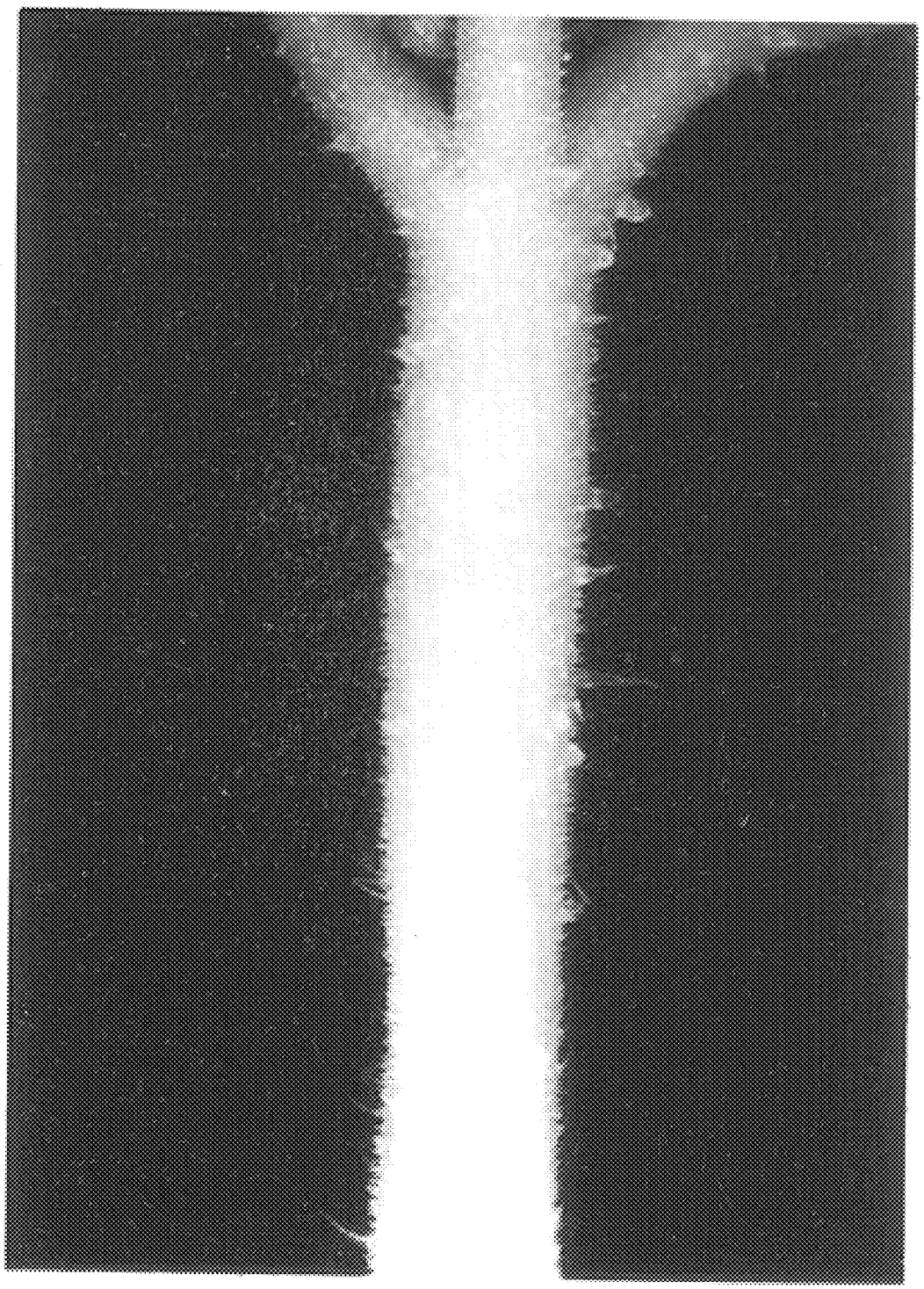
FIG. 3 is a photograph of a semispineless petiole of *C. pepo* in which the genetic factor is present in the heterozygous state.

A *C. pepo* that is "spineless" is one that has few, if any, stiff hard trichomes as compared to a *C. pepo* without the genetic factor described herein as illustrated, for example, by comparing FIGS. 1 and 2. The invention is not limited to the particular factor which has been isolated. Any species in the Cucurbita genus which expresses the spineless phenotype in an incomplete dominance form can be the source of the claimed genetic factor or its allelic complement. The genetic factor present in the *Cucurbita pepo* var. G19 seed has been deposited with the American Type Culture Collection at 10801 University Boulevard, Manassas, Va. 20110-2209 and given Accession No. 209690. These seeds can be used to raise plants having the spineless or semispineless phenotype or can be used to breed other plants in which this phenotype is desired.

The "spineless" *C. pepo* plants are characterized by a lack of irritation to the skin that results from the presence of the large stiff trichomes on a plant without the genetic factor, when the plants are handled. The trichomes on a "spineless" plant have large trichomes that are not stiff. This lack of stiffness appears to be due in part to a reduction in the size of the base of the trichome. For the purposes here, the base of the trichome is the mound of cells which can be seen to be arranged in more or less a brick-like fashion on top of the epidermis that supports a single trichome made of cells that are typically elongated and arranged in a linear manner. See FIG. 4A. When large trichomes from a spineless *C. pepo* are observed, they have bases of no more than 0.65 mm in width (as measured at "A" the major axis A on FIGS. 4A and B) and no more than 0.40 mm in width when measured at position "B" on FIG. 4B.

The genetic factor has the advantage of being readily transferred between the deposited cultivar and its related cultivars. Other C. pepo varieties in which the genetic factor could be readily introduced include, but are specifically not limited to, Zucchini Elite, Multipik, Superpik, Supersett, Midnight, Noblesse, Tigress and Jaguar (all available from Harris Moran Seed Company, Pleasanton, Calif.).

The genetic factor and the methods of the present invention can be used to modify and reduce the spines of all *C. pepo* cultivars. The methods of the present invention can be used to produce desired spineless or semispineless cultivars for commercial production. Generally, the methods involve emasculation of one parent, followed by application of pollen from the other parent to the stigma of the first parent. The crosses can be performed using either parent as the pollen parent.

A plant of the present invention can be obtained by crossing a plant homozygous for the claimed genetic factor with any cultivar lacking the factor. The plant containing the factor can be any *C. pepo* variety including a cultivar in which the factor has been previously genetically fixed.

Because the genetic factor appears to act as a single allele, the $F_1$ generation will not be spineless. Only a plant homozygous for the genetic factor will fully exhibit the spineless phenotype. This phenotype can be used to identify progeny that are homozygous for the claimed genetic factor.

After selfing the $F_1$ population, the $F_2$ generation will exhibit the phenotype in a ratio of approximately 1:3. Backcrossing $F_2$ spineless individuals with a recurrent spiney parent plant will produce the $BC_1F_1$ population. Selfing the $BC_1F_1$ population will give the $BC_1F_2$ generation. As in the $F_2$ population, the spineless trait will segregate in a ratio of about 1:3 in this population. Repeated back-crosses will produce a spineless cultivar with the characteristics of the recurrent, parent cultivar. The claimed genetic factor will thus become genetically fixed in the resulting cultivar. The trait may then be transmitted by sexual crossing to other cultivars, if desired.

Of course, other breeding schemes can be used to introduce the genetic factor into the desired cultivar. The particular scheme used is not critical to the invention, so long as the genetic factor is stably incorporated into the genome of the cultivar. For instance, a marker gene can be used. A nucleic acid probe which hybridizes to the marker gene can be used to identify the desired plants in the $F_1$ generation.

In order to determine if an unknown, spineless cultivar possesses the claimed genetic factor, a classic genetic test for allelism can be performed. The cultivar is crossed with a plant known to possess the claimed genetic factor, i.e., ATCC No. 209690 exhibiting the spineless phenotype in the homozygous state. By analyzing the resulting $F_1$ generation, the genotype of the unknown cultivar can be determined. If the unknown cultivar possesses the genetic factor, the spineless phenotype will be observed in the $F_1$ generation.

The spineless genetic factor is readily transferred from one cultivar to another. The homozygous condition is very easy to identify and environmental conditions do not affect the expression of the genetic factor. Also, the homozygote can be identified early, at least by the 4 true leaf stage and well before flowering. This makes it possible to select plants early in the greenhouse so that the selections can be transplanted.

The spineless genetic factor will advantageously be introduced into varieties that contain other desirable genetic traits such as resistance to disease, early fruit maturation, drought tolerance, fruit shape and the like. For example, the spineless genetic factor can be advantageously combined with a gene conveying resistance to zucchini yellow mosaic virus (ZYMV). At least two zucchini varieties, Tigress and Jaguar, are commercially available from Harris Moran Seed Company, Pleasanton, Calif. which serve as sources for the gene for ZYMV disease resistance.

In some cases plants heterozygous for the genetic factor will display a phenotype that has a reduction in spines sufficient to create a commercial and tactile benefit, and may in some cases be a more desirable commercial plant than one homozygous for the factor. This is more likely to be true with those varieties, such as zucchini, that tend to be less spiney to start with.

The spineless genetic factor does tend to be accompanied by fused multiple ovaries, which is a characteristic to be avoided in development of desired cultivars. Further, breeding methods must also take into account the fact that the genetic factor exhibits incomplete dominance. Heterozygous individuals can be identified with a high degree of reliability with careful examination of plants with more spiney genetic backgrounds. The following three breeding methods are recommended and take into account these issues:

Continuous Backcross Method

This method can be used to backcross the spineless phenotype into lines having heavy spines, as heterozygotes in this genetic background can be more easily detected. This method is rapid and can be done using small populations. There is, however, an increased risk over other methods that one will end up with a line having fused multiple ovaries or that one may miss selecting heterozygous individuals and have to go back to earlier generations. The method is as follows:

1. Cross a spineless line as male with the spiney parent of the desired variety (presumed to be a hybrid).
2. Cross the resulting $F_1$ with the parent of the desired variety.
3. By careful rubbing of the fingers along the petioles or visual inspection under magnification, select individuals of the $BC_1$ generation that are less spiney and backcross these individuals to the spiney recurrent parent.
4. Repeat Step 3 for the $BC_3$ and $BC_4$ generations.
5. Self pollinate less spiney individuals of the $BC_4$ generation.
6. Continue with subsequent generations by selecting individuals with good fruit type and solitary ovaries and selfing. Test crosses may be initiated at the $F_3$ generation.
7. Steps 1–6 above are followed simultaneously using the other parent of the hybrid as the recurrent parent.

Test crossing is desirable to generate new experimental hybrids. The new inbred of interest is test crossed to see if it makes a good parent line. In this particular example, at the end of the process, one should end up with desired spineless versions of the two parents of the variety of interest. Thus, one could test cross them with each other.

Continuous Backcross with Progeny/Testing of Male Segregants

This method is advantageous for adding the spineless phenotype to lines that are not so spiney. This method is rapid, assures selection of individuals carrying the spineless genetic factor and allows for selection against fused multiple ovaries. More plants, however, must be grown with this method. The method is as follows:

1. Cross a spineless line as male with the spiney parent of the desired variety.
2. Cross the resulting $F_1$ with the parents of the desired variety.
3. Identify each individual in the $BC_1$ generation and use each as a male for another backcross (to produce the $BC_2$) and for a self pollination. Individuals may be selected by carefully rubbing the fingers along the petioles or by visual inspection under magnification to identify those that are less spiney.
4. Grow out the selfed crosses and identify those segregating for spinelessness and fewer fused multiple ovaries.
5. Use those $BC_2$'s made with the desirable males in Step 3 as identified in Step 4.
6. Repeat Steps 3, 4, and 5 to obtain the $BC_3$ and $BC_4$ generations.

7. Self pollinate individuals of the $BC_4$ generation. These may be selected for fewer spines.
8. Select spineless individuals with solitary ovaries of the $BC_4F_2$ generation and self pollinate them.
9. Continue with the $F_3$ and subsequent generations by selecting individuals with good fruit type and solitary ovaries and selfing. Test crosses may be initiated at the $F_3$ generation.
10. Steps 1–9 above are followed simultaneously using the other parent of the hybrid as the recurrent parent.

Interrupted Backcross

This method is best for adding the spineless phenotype to lines that are not so spiney and selecting against fused multiple ovaries. This method is advantageous because selection for the spineless genetic factor is easy and it allows selection against fused multiple ovaries and can be done with relatively small populations. This method is, however, slower than the others.

1. Cross a spineless line as male with the spiney parent of the desired variety.
2. Cross the resulting $F_1$ with the parent of the desired variety.
3. Self pollinate less spiney individuals of the $BC_1F_2$ generation.
4. Select spineless plants with solitary ovaries in the $BC_1$ generation and use them to make another backcross.
5. Repeat Steps 2, 3, and 4 to generate the $BC_3$ and $BC_4$ generations.
6. Self pollinate individuals of the $BC_4$ generation. These may be selected for fewer spines.
7. Select spineless individuals with solitary ovaries of the $BC_4F_2$ generation and self pollinate them.
8. Continue with the $F_3$ and subsequent generations by selecting individuals with good fruit type and solitary ovaries and selfing. Test crosses may be initiated at the $F_3$ generation.
9. Steps 1–8 above are followed simultaneously using the other parent of the hybrid and the recurrent parent.

Definitions

The term "incomplete dominance" is used to refer to alleles of a heterozygote that exhibit a phenotype intermediate between that of the two corresponding homozygotes.

The term "heterozygous" refers to a condition in which a diploid individual carries different alleles at a given genetic locus.

The term "homozygous" refers to a condition in which a diploid individual carries identical alleles at a given genetic locus.

The term "genetic factor" refers to a genetic locus which is stably incorporated into the genome of a plant and which confers on the plant a characteristic phenotype.

The term "cultivar" or "variety" refers to a commercially valuable, horticulturally derived variety, as distinguished from a naturally occurring variety.

The term "genetically fixed" refers to a genetic factor which has been stably incorporated into the genome of a plant that normally does not contain the genetic factor. When genetically fixed, the genetic factor can be transmitted in a predictable manner to other plants by sexual crosses.

The terms "derived from" means originated directly or indirectly from the specified source.

The term "recurrent parent" in plant breeding refers to the parent plant that is repeatedly used in a sequence of backcrossing, which has characteristics desirable for the plant one is attempting to obtain.

The term "isogenic" refers to one or more organisms which have the same genotypes.

The term "allelic complement" refers to the case where one allele is the complement to another allele because they both give rise to the same phenotype.

The following experimental results are offered by way of example and not to be construed as a limitation on the claims.

EXAMPLES

The plant populations I obtained were are all generated by selfing individuals and the results are presented in Table 1 and described below. Assuming that a single recessive gene controls spinelessness, we would expect that 25% of the plants of an $F_2$ population derived from the self pollination of a heterozygous individual would be spineless. This predicted number is that listed in the "EXPECTED SPINELESS" column of Table 1. In Table 1, "Ref" references my internal data collection number.

P11, P2, B5 and G8 are all spiney inbreds. P11 is yellow-crookneck squash. P2, B5 and G8 are yellow straightneck squash. All of these have the precocious yellow (B) gene.

The $F_2$'s (lines 2 through 20 of Table 1) are self crosses of $F_1$'s made of "P3," the original spineless C. pepo line obtained from the male of the variety, Multipik (Harris Moran Seed Company), and 1 spiney inbred of Multipik, 1 spiney inbred of Superpik and 2 spiney inbreds of Supersett (all of Harris Moran Seed Company). So, each population should segregate for spineless, since the parent should be heterozygous. The cross with "P11" (lines 2 and 3 of Table 1) yielded fewer spineless plants than expected, while the other crosses were relatively close to the expected number. The reason for the discrepancy is unknown, but it could be due to differential pollen vigor or survival.

The $BC_1F_2$'s (lines 24 through 67 of Table 1) were derived from self pollinations of first backcrosses. The first backcross, assuming a single gene, should segregate in a 1:1 ratio homozygous spiney to heterozygous. Therefore, a random selection of individuals should yield 2 kinds of populations: those which are 100% spiney and those which are 75% spiney and 25% spineless. Although the spineless genetic factor exhibits a spineless phenotype in the homozygous state, it is possible to select plants that are heterozygous and less spiney in a backcross population. Out of 28 $BC_1F_2$ populations, only 2 (lines 38 and 49 of Table 1) did not segregate spineless. This indicates that selection was successful, otherwise about 14 of these populations would not segregate. In general, ratios of the segregating populations came close to the expected ratios.

As further evidence for the existence of the single recessive gene characterization: the $F_1$'s were all spiney; and $F_3$'s derived from spineless $F_2$'s were all spineless. The only exception was plot 3845 (Ref. 11a of Table 1), an $F_3$ which had 2 spiney and 2 spineless plants which may have been due to an inadequate pollination.

No backcrosses were made to spineless parents.

TABLE 1

GENETIC RATIOS OF SPINELESS GENETIC FACTOR

| GENERATION | TOTAL PLANTS | OBSERVED SPINELESS | EXPECTED SPINELESS | COMMENTS |
|---|---|---|---|---|
| 1 P3 × P11 | | Ref. 4 | | |
| 2 206200000-1 F$_2$ | 16 | 1 | 4 | * |
| 3 206200000-2 F$_2$ | 16 | 0 | 4 | * |
| 4 TOTAL | 32 | 1 | 8 | * |
| 5 P2 × P3 | | Ref. 4 | | |
| 6 206300000-1 F$_2$ | 8 | 0 | 2 | |
| 7 206300000-2 F$_2$ | 8 | 4 | 2 | |
| 8 206300000-3 F$_2$ | 8 | 1 | 2 | |
| 9 206300000-4 F$_2$ | 8 | 1 | 2 | |
| 10 TOTAL | 32 | 8 | | |
| 11 B5 × P3 | | Ref. 4 | | |
| 12 206400000-1 F$_2$ | 8 | 3 | 2 | |
| 13 206400000-2 F$_2$ | 8 | 1 | 2 | |
| 14 206400000-3 F$_2$ | 8 | 3 | 2 | |
| 15 206400000-4 F$_2$ | 8 | 2 | 2 | |
| 16 TOTAL | 32 | 9 | 8 | |
| 17 G8 × P3 | | Ref. 4 | | |
| 18 206500000-1 F$_2$ | 8 | 2 | 2 | |
| 19 206500000-2 F$_2$ | 8 | 2 | 2 | |
| 20 206500000-3 F$_2$ | 8 | 3 | 2 | |
| 21 TOTAL | 24 | 7 | 6 | |
| 22 | | | | |
| 23 | | | | |
| 24 B5 × P3 | | Ref. 6 | | |
| 25 382200000-1 BC1FC | 16 | 3 | 4 | |
| 26 382200000-2 BC1F2 | 16 | 5 | 4 | |
| 27 382200000-3 BC1F2 | 16 | 3 | 4 | |
| 28 382200000-4 BC1F2 | 16 | 2 | 4 | |
| 29 TOTAL | 64 | 13 | 16 | |
| 30 B5 × P3 | | Ref. 6 | | |
| 31 382300000-1 BC1F2 | 16 | 4 | 4 | |
| 32 382300000-2 BC1F2 | 14 | 4 | 3.5 | |
| 33 382300000-3 BC1F2 | 7 | 3 | 1.75 | |
| 34 382300000-4 BC1F2 | 14 | 2 | 3.5 | |
| 35 TOTAL | 51 | 13 | 12.75 | |
| 36 B5 × P3 | | Ref. 6 | | |
| 37 382400000-1 BC1F2 | 16 | 2 | 4 | |
| 38 382400000-2 BC1F2 | 10 | 0 | 2.5 | |
| 39 382400000-3 BC1F2 | 8 | 1 | 2 | |
| 40 382400000-4 BC1F2 | 8 | 3 | 2 | |
| 41 TOTAL | 42 | 6 | 10.5 | |
| 42 B5 × P3 | | Ref. 6 | | |
| 43 382500000-1 BC1F2 | 8 | 2 | 2 | |
| 44 382500000-2 BC1F2 | 16 | 4 | 4 | |
| 45 TOTAL | 24 | 6 | 6 | |
| 46 G8 × P3 | | Ref. 6 | | |
| 47 383100000-1 BC1F2 | 16 | 6 | 4 | |
| 48 383100000-2 BC1F2 | 16 | 4 | 4 | |
| 49 383100000-4 BC1F2 | 16 | 0 | 4 | |
| 50 383100000-5 BC1F2 | 16 | 5 | 4 | |
| 51 383100000-6 BC1F2 | 16 | 5 | 4 | |
| 52 TOTAL | 80 | 20 | 20 | |
| 53 P3 × P11 | | Ref. 6 | | |
| 54 383700000-1 BC1F2 | 16 | 3 | 4 | |
| 55 383700000-2 BC1F2 | 16 | 2 | 4 | |
| 56 TOTAL | 32 | 5 | 8 | |
| 57 P3 × P11 | | Ref. 6 | | |
| 58 383800000-1 BC1F2 | 16 | 2 | 4 | |
| 59 383800000-2 BC1F2 | 16 | 2 | 4 | |
| 60 383800000-3 BC1F2 | 16 | 4 | 4 | |
| 61 383800000-4 BC1F2 | 16 | 3 | 4 | |
| 62 TOTAL | 64 | 11 | 16 | |
| 63 P3 × P11 | | Ref. 6 | | |

TABLE 1-continued

GENETIC RATIOS OF SPINELESS GENETIC FACTOR

| GENERATION | TOTAL PLANTS | OBSERVED SPINELESS | EXPECTED SPINELESS | COMMENTS |
|---|---|---|---|---|
| 64 383900000-1 BC1F2 | 16 | 2 | 4 | |
| 65 P3 × P11 | | Ref. 6 | | |
| 66 38400000-1 BC1F2 | 8 | 3 | 2 | |
| 67 38400000-2 BC1F2 | 16 | 5 | 4 | |
| 68 TOTAL | 24 | 8 | 6 | |

For this cross, it has been demonstrated that spininess of the petioles of summer squash (*C. pepo*, L.) is heritable, and that inheritance is qualitative with no maternal effects. The spiney type is dominant over smooth in $F_1$ and $F_2$ populations.

What is claimed is:

1. A *Cucurbita pepo* cultivar that is homozygous for an allelic DNA genetic factor which is incompletely dominant in the heterozygous state and confers on a *Cucurbita pepo* plant a spineless phenotype such that when the plant is crossed with a plant named G19 with seed having ATCC No. 209690, the first generation progeny exhibit a spineless phenotype.

2. A cultivar of claim 1 derived from a plant named G19 with seed having ATCC No. 209690.

3. A cultivar of claim 1 that further exhibits disease resistance to zucchini yellow mosaic virus.

4. A cultivar of claim 1 isogenic to those of G19 with seed having ATCC No. 209690.

5. A *Cucurbita pepo* cultivar heterozygous for an allelic genetic factor which is incompletely dominant in the heterozygous state and in the homozygous state confers on a *C. pepo* plant a spineless phenotype such that when a plant with the genetic factor in a homozygous state is crossed with a plant named G19 with seed having ATCC No. 209690, the first generation progeny exhibit a spineless phenotype.

6. A *Cucurbita pepo* cultivar seed homozygous for an allelic genetic factor which is incompletely dominant in the heterozygous state and confers on a *Cucurbita pepo* plant a spineless phenotype such that when a plant arising from the seed is crossed with a plant named G19 with seed having ATCC No. 209690, the first generation progeny exhibit a spineless phenotype.

7. A seed of claim 6 derived from a plant named G19 with seed having ATCC No. 209690.

8. A seed of claim 6 that further gives rise to a plant which exhibits disease resistance to zucchini yellow mosaic virus.

9. A seed of claim 6 isogenic to those of G19 having ATCC No. 209690.

10. A seed which gives rise to a *Cucurbita pepo* cultivar heterozygous for an allelic genetic factor which is incompletely dominant in the heterozygous state and in the hornozygous state confers on a *C. pepo* plant a spineless phenotype such that when a plant with the genetic factor in a homozygous state is crossed with a plant named G19 with seed having ATCC No. 209690, the first generation progeny exhibit a spineless phenotype.

11. A method for introducing into a *Cucurbita pepo* plant an allelic genetic factor which which is incompletely dominant in the heterozygous state and in the homozygous state confers on a *Cucurbita pepo* plant a spineless phenotype, the method comprising:

(a) crossing a *C. pepo* variety of interest with that of cultivar G19 with seed having ATCC No. 209690;

(b) then backcrossing the progeny with the variety of interest and then self-crossing the resulting generation; and (c) selecting for those plants exhibiting a spineless phenotype.

* * * * *